(12) United States Patent
Stanhope et al.

(10) Patent No.: US 10,820,472 B2
(45) Date of Patent: Nov. 3, 2020

(54) SYSTEM AND METHOD FOR DETERMINING SOIL PARAMETERS OF A FIELD AT A SELECTED PLANTING DEPTH DURING AGRICULTURAL OPERATIONS

(71) Applicant: CNH Industrial America LLC, New Holland, PA (US)

(72) Inventors: Trevor Stanhope, Darien, IL (US); Christopher Barrick, Morton, IL (US)

(73) Assignee: CNH Industrial America LLC, New Holland, PA (US)

( * ) Notice: Subject to any disclaimer, the term of this patent is extended or adjusted under 35 U.S.C. 154(b) by 169 days.

(21) Appl. No.: 16/134,580

(22) Filed: Sep. 18, 2018

(65) Prior Publication Data
US 2020/0084953 A1    Mar. 19, 2020

(51) Int. Cl.
*A01B 63/111*    (2006.01)
*A01B 63/32*    (2006.01)
(Continued)

(52) U.S. Cl.
CPC ............ *A01B 63/32* (2013.01); *A01B 79/005* (2013.01); *G01N 33/24* (2013.01); *A01B 49/027* (2013.01); *G01N 2033/245* (2013.01)

(58) Field of Classification Search
CPC ..... A01B 49/06; A01B 49/027; A01B 63/002; A01B 63/16; A01B 63/32; A01B 63/145;
(Continued)

(56) References Cited

U.S. PATENT DOCUMENTS 6,484,099 B1     11/2002   Holzer-Popp et al.
6,484,652 B1 *   11/2002   Colburn, Jr. ......... A01B 79/005
                                                         111/118
(Continued)

FOREIGN PATENT DOCUMENTS

AU     2017101749 A    2/2018
CN      205157419 U    4/2016
(Continued)

OTHER PUBLICATIONS

Metternicht et al., Remote Sensing of Soil Salinity: Poetentials and Constraints, Remote Sensing Environment vol. 85, 2003, pp. 1-20.

*Primary Examiner* — Robert E Pezzuto
(74) *Attorney, Agent, or Firm* — Rebecca L. Henkel; Rickard K. DeMille

(57) ABSTRACT

In one aspect, a system for determining soil parameters of a field across which an agricultural implement is being moved may include a sensor mounted on a ground engaging member. As such, the sensor may be configured to capture data indicative of a soil parameter of soil within the field. Furthermore, the system may include a controller configured to receive an input indicative of a selected planting depth for the field. Moreover, the controller may be configured to control an operation of an actuator in a manner that adjusts the penetration depth of the ground engaging member such that the sensor is positioned at the selected planting depth. Additionally, the controller may be configured to determine the soil parameter of the soil within the field at the selected planting depth based on the data received from the sensor.

14 Claims, 5 Drawing Sheets

(51) Int. Cl.
   *A01B 79/00* (2006.01)
   *G01N 33/24* (2006.01)
   *A01B 49/02* (2006.01)

(58) Field of Classification Search
   CPC ..... A01B 63/008; A01B 79/005; A01C 5/064; A01C 7/203; A01C 7/205; A01C 21/00; A01C 14/00; G01C 21/3461; G01N 33/24; G05D 1/0246
   USPC ..... 56/10.2 A–10.2 G, 10.2 R; 111/118, 119, 111/200; 172/2–11; 701/50
   See application file for complete search history.

(56) References Cited

U.S. PATENT DOCUMENTS

| | | | |
|---|---|---|---|
| 6,596,996 B1 | 7/2003 | Stone et al. | |
| 7,280,204 B2 | 10/2007 | Robinson et al. | |
| 7,417,731 B1 | 8/2008 | Masten | |
| 8,451,449 B2 | 5/2013 | Holland | |
| 8,451,527 B2 | 5/2013 | Bodkin | |
| 8,816,262 B2 | 8/2014 | Holland | |
| 9,285,501 B2 | 3/2016 | Christy et al. | |
| 9,629,304 B2* | 4/2017 | Zielke | A01C 21/00 |
| 9,651,536 B1 | 5/2017 | Lund et al. | |
| 9,743,574 B1 | 8/2017 | Maxton et al. | |
| 10,165,725 B2* | 1/2019 | Sugumaran | G01C 21/3461 |
| 10,537,055 B2* | 1/2020 | Gresch | A01C 7/203 |
| 2011/0242328 A1 | 10/2011 | Twede et al. | |
| 2013/0180742 A1* | 7/2013 | Wendte | A01B 63/1145 172/4 |
| 2017/0122889 A1 | 5/2017 | Weindorf et al. | |
| 2017/0131718 A1 | 5/2017 | Matsumura et al. | |
| 2017/0223947 A1 | 8/2017 | Gall et al. | |

FOREIGN PATENT DOCUMENTS

| | | |
|---|---|---|
| RU | 2554987 C2 | 7/2015 |
| RU | 2650534 C2 | 4/2018 |
| WO | WO2009/153304 A1 | 12/2009 |

* cited by examiner

SYSTEM AND METHOD FOR DETERMINING SOIL PARAMETERS OF A FIELD AT A SELECTED PLANTING DEPTH DURING AGRICULTURAL OPERATIONS

FIELD OF THE INVENTION

The present disclosure generally relates to agricultural implements and, more particularly, to systems and methods for determining soil parameters of a field across which an agricultural implement is being moved at a selected planting depth during agricultural operations.

BACKGROUND OF THE INVENTION

It is well known that, to attain the best agricultural performance from a field, a farmer must cultivate the soil, typically through a tillage operation. Modern farmers perform tillage operations by pulling a tillage implement behind an agricultural work vehicle, such as a tractor. Tillage implements typically include a plurality of ground engaging tools, such as harrow discs, shanks, leveling discs, tines, rolling baskets, and/or the like, which loosen and/or otherwise agitate the soil to prepare the soil for subsequent planting operations.

Upon completion of the tillage operation, it is generally desirable that the soil within the field have the appropriate soil tilth (i.e., the physical condition of the soil in relation to its suitability for planting or growing a crop), which is defined by certain parameters (e.g., aeration, aggregates, moisture, temperature, residue content, and/or the like) at the depth at which seeds will be placed during the subsequent planting operations. In this regard, it may be necessary to adjust one or more operating parameters of the tillage implement during the tillage operation to ensure that the field has such soil parameters. However, the tillage implement operator is unable to determine the parameters of the soil at the planting depth while performing the tillage operation.

Accordingly, an improved system and method for determining soil parameters of a field across which an agricultural implement is being moved, such as at a selected planting depth within the field, would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to a system for determining soil parameters of a field across which an agricultural implement is being moved. The system may include a ground engaging member configured to penetrate soil within the field and an actuator configured to adjust a penetration depth of the ground engaging member. The system may also include a sensor mounted on the ground engaging member, with the sensor configured to capture data indicative of a soil parameter of soil within the field. Furthermore, the system may include a controller communicatively coupled to the sensor. The controller may be configured to receive an input indicative of a selected planting depth for the field. Moreover, the controller may be configured to control an operation of the actuator in a manner that adjusts the penetration depth of the ground engaging member such that the sensor is positioned at the selected planting depth. Additionally, the controller may be configured to determine the soil parameter of the soil within the field at the selected planting depth based on the data received from the sensor.

In another aspect, the present subject matter is directed to a method for determining soil parameters of a field across which an agricultural implement is being moved. The agricultural implement may include a ground engaging member and a sensor mounted on the ground engaging member. The method may include receiving, with a computing device, an input indicative of a selected planting depth for the field. The method may also include controlling, with the computing device, an operation of an actuator in a manner that adjusts a penetration depth of the ground engaging member such that the sensor is positioned at the selected planting depth. Furthermore, the method may include determining, with the computing device, a soil parameter of soil within the field at the selected planting depth based on data received from the sensor.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

DETAILED DESCRIPTION OF THE DRAWINGS

Figure 1:
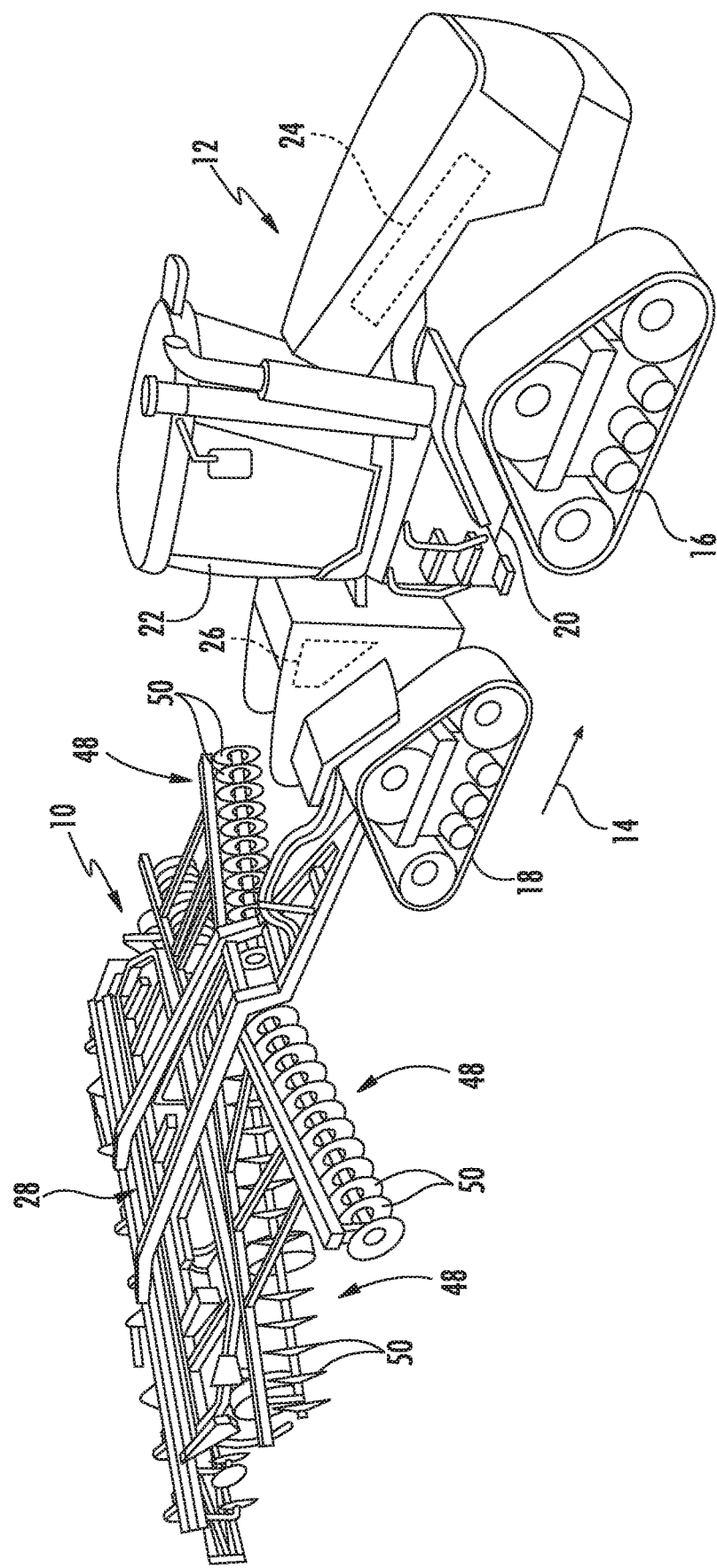
FIG. 1 illustrates a perspective view of one embodiment of an agricultural implement coupled to a work vehicle in accordance with aspects of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for determining soil parameters of a field across which an agricultural implement is being moved. Specifically, in several embodiments, a controller of the disclosed system may be configured to receive an input indicative of a selected planting depth for the field. For example, in one embodiment, the controller may receive the input from a user interface of the system. As such, the controller may control the operation of an actuator of the implement in a manner the adjusts the penetration depth of a ground engaging member of the implement such that a sensor mounted on the ground engaging member is positioned at the selected planting depth. In this regard, the controller may be configured to determine or estimate one or more soil parameters of the soil within the field at the selected planting depth based on data received from the sensor. For example, such soil parameters may include the presence and stability of soil aggregates, the degree of aeration, the presence and/or amount of residue, the amount of organic matter, the moisture content of the soil, and/or a temperature of the soil. Thereafter, in the event that the determined soil parameter(s) exceeds or falls below an associated threshold soil parameter value, the controller may be configured to initiate one or more control actions. Such control action(s) may generally he associated with adjusting the soil parameter(s). For example, in one embodiment, the control action(s) may include adjusting one or more operating parameters of the implement, such as the ground speed of the implement, the penetration depth of a ground engaging shank(s) of the implement, and/or the angle of a disc gang(s) of the implement.

Figure 2:
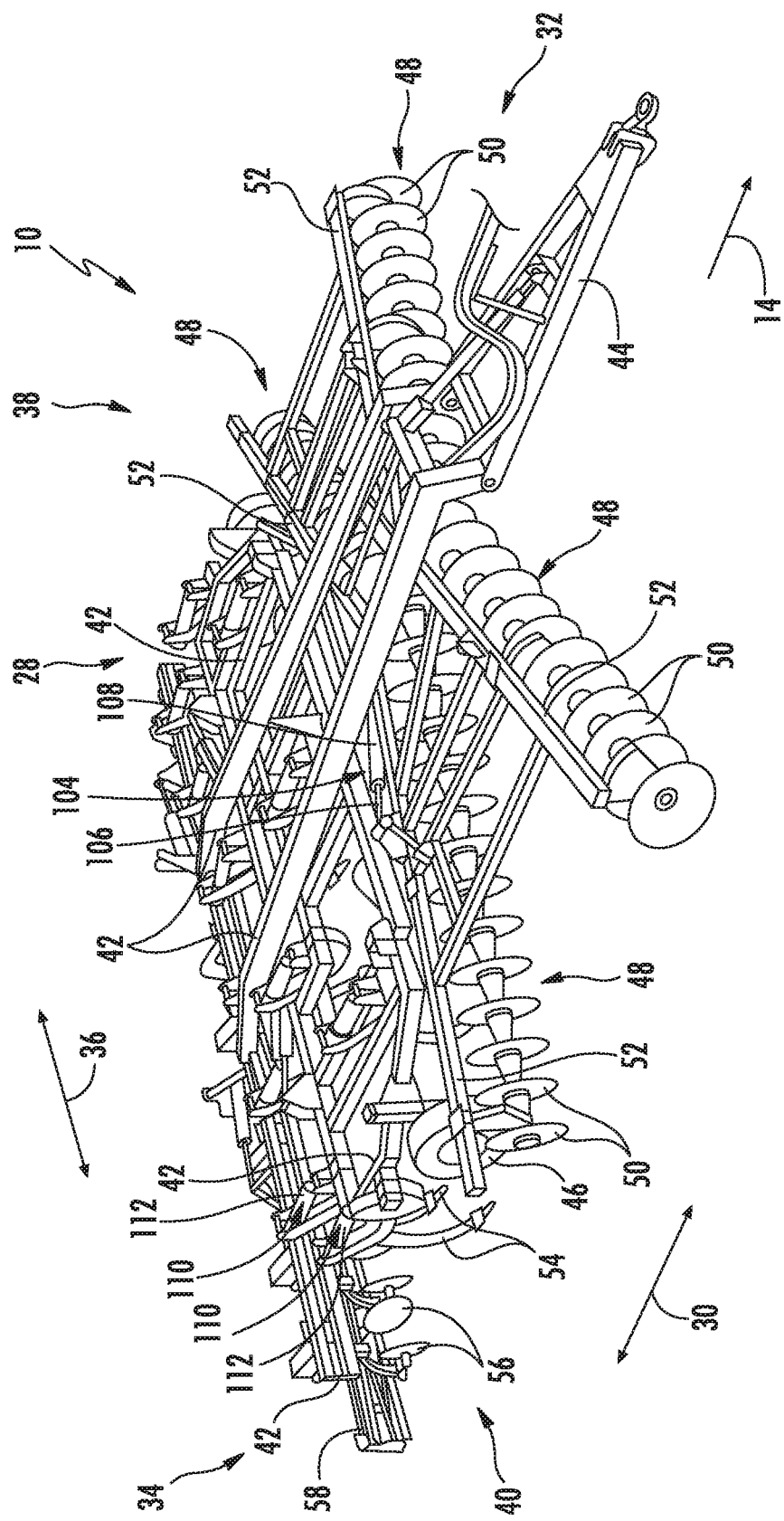
FIG. 2 illustrates an alternative perspective view of an agricultural implement in accordance with aspects of the present subject matter, particularly illustrating various components of the implement.

Referring now to the drawings, FIGS. 1 and 2 illustrate differing perspective views of one embodiment of an agricultural implement 10 in accordance with aspects of the present subject matter. Specifically, FIG. 1 illustrates a perspective view of the agricultural implement 10 coupled to a work vehicle 12. Additionally, FIG. 2 illustrates a perspective view of the implement 10, particularly illustrating various components of the implement 10.

In general, the implement 10 may be configured to be towed across a field in a direction of travel (e.g., as indicated by arrow 14 in FIG. 1) by the work vehicle 12. As shown, the implement 10 may be configured as a tillage implement, and the work vehicle 12 may be configured as an agricultural tractor. However, in other embodiments, the implement 10 may be configured as any other suitable type of implement, such as a seed-planting implement, a fertilizer-dispensing implement, and/or the like. Similarly, the work vehicle 12 may be configured as any other suitable type of vehicle, such as an agricultural harvester, a self-propelled sprayer, and/or the like.

As shown in FIG. 1, the work vehicle 12 may include a pair of front track assemblies 16 (one is shown), a pair of rear track assemblies 18 (one is shown), and a frame or chassis 20 coupled to and supported by the track assemblies 16, 18. An operator's cab 22 may be supported by a portion of the chassis 20 and may house various input devices (e.g., a user interface 102 shown in FIG. 4) for permitting an operator to control the operation of one or more components of the work vehicle 12 and/or one or more components of the implement 10. Additionally, as is generally understood, the work vehicle 12 may include an engine 24 and a transmission 26 mounted on the chassis 20. The transmission 26 may be operably coupled to the engine 24 and may provide variably adjusted gear ratios for transferring engine power to the track assemblies 16, 18 via a drive axle assembly (not shown) (or via axles if multiple drive axles are employed).

As shown in FIGS. 1 and 2, the implement 10 may include an implement frame 28. As shown in FIG. 2, the frame 28 may extend along a longitudinal direction 30 between a forward end 32 and an aft end 34. The frame 28 may also extend along a lateral direction 36 between a first side 38 and a second side 40. In this respect, the frame 28 generally includes a plurality of structural frame members 42, such as beams, bars, and/or the like, configured to support or couple to a plurality of components. Furthermore, a hitch assembly 44 may be connected to the frame 28 and configured to couple the implement 10 to the work vehicle 12. Additionally, a plurality of wheels 46 (one is shown) may be coupled to the frame 28 to facilitate towing the implement 10 in the direction of travel 14.

In several embodiments, the frame 28 may be configured to support one or more gangs or sets 48 of disc blades 50. Each disc blades 50 may, in turn, be configured to penetrate into or otherwise engage the soil as the implement 10 is being pulled through the field. In this regard, the various disc gangs 48 may be oriented at an angle relative to the direction of travel 14 to promote more effective tilling of the soil. In the embodiment shown in FIGS. 1 and 2, the implement 10 includes four disc gangs 48 supported on the frame 28 adjacent to its forward end 32. However, it should be appreciated that, in alternative embodiments, the implement 10 may include any other suitable number of disc gangs 48, such as more or fewer than four disc gangs 48. Furthermore, in one embodiment, the disc gangs 48 may be mounted to the frame 28 at any other suitable location, such as adjacent to its aft end 34.

Moreover, in several embodiments, the implement 10 may include a plurality of disc gang actuators 104 (one is shown), with each actuator 104 being configured to move or otherwise adjust the orientation or position of one of the disc gangs 48 relative to the implement frame 28. For example, as shown in the illustrated embodiment, a first end of each actuator 104 (e.g., a rod 106 of the actuator 104) may be coupled to a support arm 52 of the corresponding disc gang 44, while a second end of each actuator 104 (e.g., the cylinder 108 of the actuator 104) may be coupled to the frame 28. The rod 106 of each actuator 104 may be configured to extend and/or retract relative to the corresponding cylinder 108 to adjust the angle of the corresponding disc gang 48 relative to a lateral centerline (not shown) of the frame 28 and/or the penetration depth of the associated disc blades 50. In the illustrated embodiment, each actuator 104 corresponds to a fluid-driven actuator, such as a hydraulic or pneumatic cylinder. However, it should be appreciated that each actuator 104 may correspond to any other suitable type of actuator, such as an electric linear actuator.

In one embodiment, the frame 28 may be configured to support a plurality of shanks 54 configured to rip or otherwise till the soil as the implement 10 is towed across the field. More specifically, the shanks 54 may be configured to be pivotally mounted to the frame 28 in a manner that permits the penetration depths of the shanks 54 to be adjusted. In this regard, a plurality of shank actuators 110 may be configured to move or otherwise adjust the orientation or position of a corresponding shank 54 relative to the implement frame 28. For example, as shown in the illustrated embodiment, a first end of each actuator 110 (e.g., a rod (not shown) of the actuator 110) may be coupled to the corresponding shank 54, while a second end of each actuator 110 (e.g., the cylinder 112 of the actuator 110) may be coupled to the frame 28. The rod of each actuator 110 may be configured to extend and/or retract relative to the corresponding cylinder 112 to adjust the penetration depth of the corresponding shank 54. In the illustrated embodiment, each actuator 110 corresponds to a fluid-driven actuator, such as a hydraulic or pneumatic cylinder. However, it should be appreciated that each actuator 110 may correspond to any other suitable type of actuator, such as an electric linear actuator.

Additionally, as shown, in one embodiment, the implement frame 28 may be configured to support other ground engaging tools. For instance, in the illustrated embodiment, the frame 28 is configured to support a plurality of leveling blades 56 and rolling (or crumbler) basket assemblies 58. However, in other embodiments, any other suitable ground-engaging tools may be coupled to and supported by the implement frame 28, such as a plurality closing discs.

Figure 3:
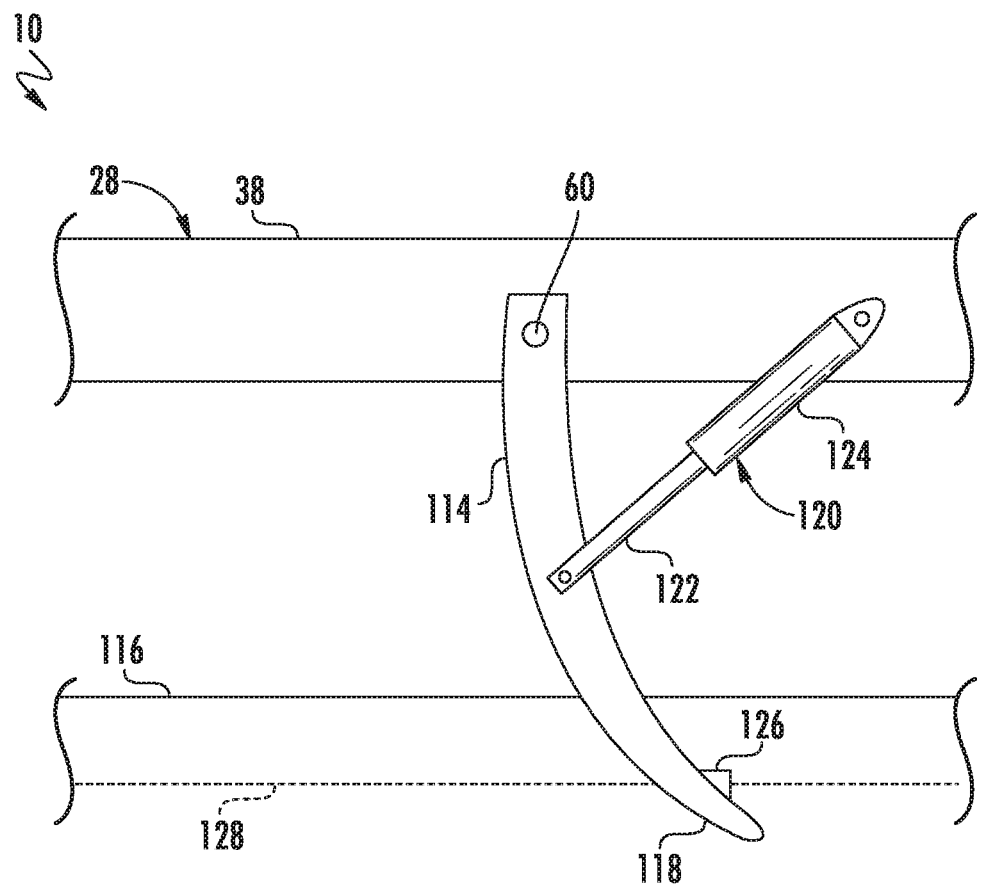
FIG. 3 illustrates an enlarged, partial side view of an agricultural implement in accordance with aspects of the present subject matter, particularly illustrating a ground engaging member of the implement.

Referring now to FIG. 3, an enlarged, partial side view of the implement 10 is illustrated in accordance with aspects of the present subject matter. As shown, in several embodiments, the implement 10 may include a ground engaging member 114 configured to penetrate or otherwise engage the soil as the implement 10 is moved across the field. In this regard, one end of the ground engaging member 114 may include a tip portion 118 configured to penetrate the soil surface (e.g., as indicated by line 116 in FIG. 3), while an opposed end of the ground engaging member 114 may be pivotally coupled to the frame 28, such as at a pivot point 60. As such, the ground engaging member 114 may be configured to pivot relative to the frame 28 in a manner that adjusts its penetration depth. In the illustrated embodiment, the ground engaging member 114 has a generally arcuate shape. However, it should be appreciated that, in alternative embodiments, the ground engaging member 114 may have any other suitable configuration. Furthermore, although one ground engaging member 114 is illustrated in FIG. 3, the implement 10 may include any other suitable number of ground engaging members 114, such as two or more ground engaging members 114.

In several embodiments, the implement 10 may include a ground engaging member actuator 120 configured to move or otherwise adjust the orientation or position of the ground engaging member 120 relative to the implement frame 28. For example, as shown in the illustrated embodiment, a first end of the actuator 120 (e.g., a rod 122 of the actuator 120) may be coupled to the ground engaging member 114, while a second end of the actuator 104 (e.g., the cylinder 124 of the actuator 120) may be coupled to the frame 28. The rod 122 of each actuator 120 may be configured to extend and/or retract relative to the corresponding cylinder 124 to adjust the penetration depth of the ground engaging member 114. In the illustrated embodiment, each actuator 120 corresponds to a fluid-driven actuator, such as a hydraulic or pneumatic cylinder. However, it should be appreciated that each actuator 120 may correspond to any other suitable type of actuator, such as an electric linear actuator.

In accordance with aspects of the present subject matter, the implement 10 may include a sensor 126 configured to capture data indicative of one or more soil parameters of the soil within the field. Specifically, in several embodiments, the sensor 126 may be mounted or otherwise installed on the ground engaging member 114. For example, as shown in in FIG. 3, the sensor 126 may be mounted on the tip portion 118 of the ground engaging member 114 such that the sensor 126 is positioned below the soil surface 116 when the implement 10 is moved across the field. In this regard, the sensor 126 may be configured to capture data indicative of the soil parameter(s) at a sensor penetration depth (e.g., as indicated by dashed line 128 in FIG. 3). As will be described below, the ground engaging actuator 120 may be configured to adjust the position of the ground engaging member 114 relative to the implement frame 28 such that the sensor penetration depth 128 of the sensor 126 corresponds to a selected planting depth of seeds or other agricultural products in a subsequent planting operation. However, in alternative embodiments, the sensor 126 may be mounted at any other suitable location on the ground engaging shank 114 that permits the sensor 126 to capture soil parameter data at the selected planted depth.

It should be appreciated that the sensor 126 may correspond to any suitable sensing device configured to capture data indicative of the soil parameter(s). For example, in one embodiment, the sensor 126 may correspond to an optical sensor configured to emit one or more wavelengths of visible or near-infrared light for reflection off of the soil and detect one or more characteristics of the reflected light (e.g., a two-dimensional image, intensity, and/or phase-shift of particular wavelength, and/or the like). Such characteristics may, in turn, be indicative of the soil parameter(s). In another embodiment, the sensor 126 may correspond to a multispectral sensor configured to detect one or more spectral bands of the electromagnetic radiation reflected off of the soil (e.g. visible light, near-infrared light, mid-infrared light, ultraviolet light, and/or the like). One or more characteristics of the spectral bands may, in turn, be indicative of the soil parameter(s). In a further embodiment, the sensor 126 may correspond to a dielectric sensor configured to detect the dielectric permittivity of the soil, with the permittivity being indicative of the soil parameter(s). However, the sensor 126 may be any suitable sensing device that detects visible light, near-infrared light, single wavelengths, discrete spectra, continuous spectra, one-dimensional data, two-dimensional images, and/or three dimensional images. Furthermore, the sensor 126 may be a passive or emissive device.

Furthermore, it should be appreciated that the configuration of the implement 10 described above and shown in FIGS. 1-3 is provided only to place the present subject matter in an exemplary field of use. Thus, it should be appreciated that the present subject matter may be readily adaptable to any manner of implement configuration. For example, in one embodiment, the implement 10 may be configured as a field cultivator.

Figure 4:
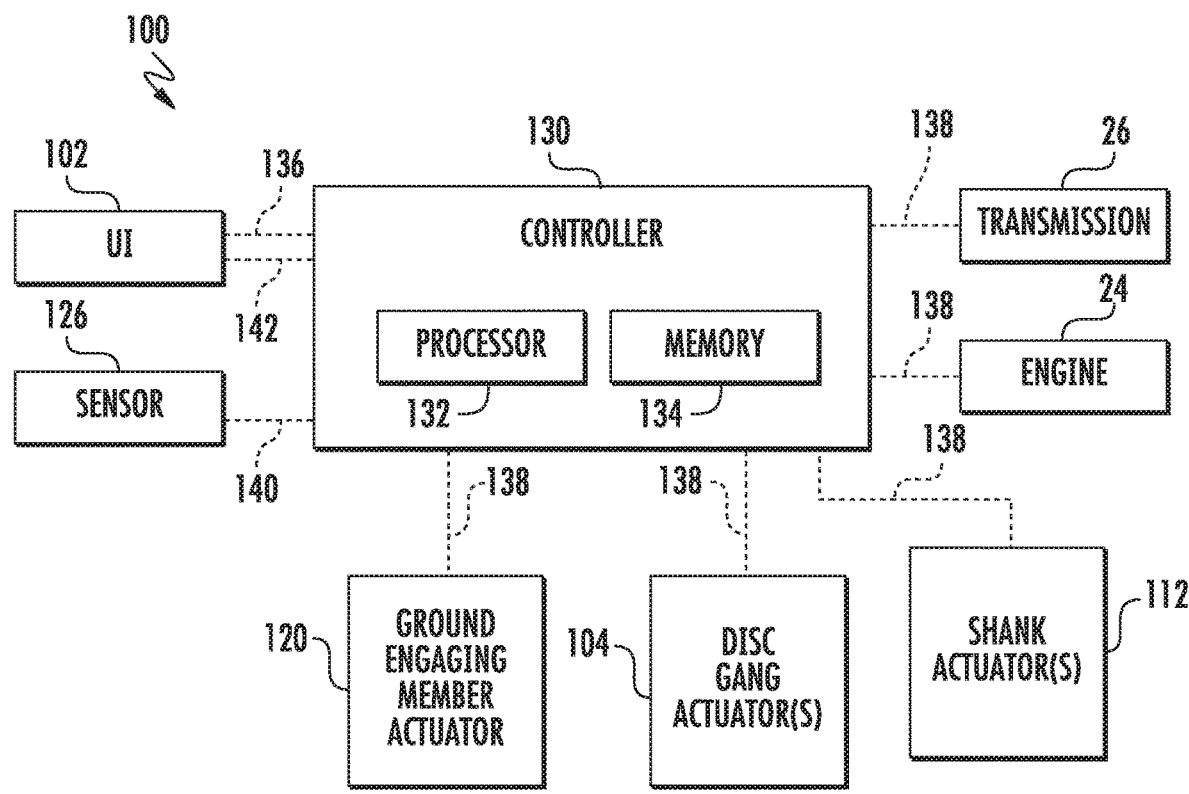
FIG. 4 illustrates a schematic view of one embodiment of a system for determining soil parameters of a field across which an agricultural implement is being moved in accordance with aspects of the present subject matter.

Referring now to FIG. 4, a schematic view of one embodiment of a system 100 for determining soil parameters of a field across Which an agricultural implement is being moved is illustrated in accordance with aspects of the present subject matter. In general, the system 100 will be described herein with reference to the agricultural implement 10 and the work vehicle 12 described above with reference to FIGS. 1-3. However, it should be appreciated by those of ordinary skill in the art that the disclosed system 100 may generally be utilized with agricultural implements having any other suitable implement configuration and/or work vehicles having any other suitable vehicle configuration.

As shown in FIG. 4, the system 100 may include a controller 130 configured to electronically control the operation of one or more components of the implement 10 and/or the work vehicle 12. In general, the controller 130 may comprise any suitable processor-based device known in the art, such as a computing device or any suitable combination of computing devices. Thus, in several embodiments, the controller 130 may include one or more processor(s) 132 and associated memory device(s) 134 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 134 of the controller 130 may generally comprise memory element(s) including, but not limited to, a computer readable medium (e.g., random access memory (RAM)), a computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 134 may generally be configured to store suitable computer-readable instructions that, when implemented by the processor(s) 132, configure the controller 130 to perform various computer-implemented functions, such as one or more aspects of the method 200 described below with reference to FIG. 5. In addition, the controller 130 may also include various other suitable components, such as a communications circuit or module, one or more input/output channels, a data/control bus and/or the like.

It should be appreciated that the controller 130 may correspond to an existing controller of the implement 10 or the work vehicle 12 or the controller 130 may correspond to a separate processing device. For instance, in one embodiment, the controller 130 may form all or part of a separate plug-in module that may be installed within the implement 10 or the work vehicle 12 to allow for the disclosed system and method to be implemented without requiring additional software to be uploaded onto existing control devices of the implement 10 or the work vehicle 12.

Furthermore, in one embodiment, the system 100 may also include the user interface 102. More specifically, the user interface 102 may be configured to receive input (e.g., input associated with the selected planting depth of seeds or other agricultural products in subsequent planting operations) from the operator of the implement 10. As such, the user interface 102 may include one or more input devices (not shown), such as touchscreens, keypads, touchpads, knobs, buttons, sliders, switches, mice, microphones, and/or the like, which are configured to receive such inputs. In addition, some embodiments of the user interface 102 may include one or more feedback devices (not shown), such as display screens, speakers, warning lights, and/or the like, which are configured to communicate feedback to the operator. In one embodiment, the user interface 102 may be positioned within a cab of a work vehicle configured to tow the implement 10 across the field. However, in alternative embodiments, the user interface 102 may have any suitable configuration and/or be positioned in any other suitable location.

In several embodiments, the controller 130 may be configured to receive an input indicative of a selected planting depth for the field. In general, the selected planting depth is the depth below the soil surface 116 at which seeds or other agricultural substances (e.g., fertilizer) are deposited or otherwise placed during a subsequent planting operation(s). More specifically, the controller 130 may be communicatively coupled to the user interface 102 via a wired or wireless connection to allow operator input signals (e.g., indicated by dashed line 136 in FIG. 4) to be transmitted from the user interface 102 to the controller 130. In this regard, the operator of the implement 10 may provide the selected planting depth to the user interface 102, such as via the one or more input devices. The selected planting depth may, in turn, be transmitted to the controller 130 via, user input signals 136.

Moreover, in several embodiments, the controller 130 may be configured to control the operation of ground engaging member actuator 120 such that the sensor 126 is positioned at the selected planting depth. Specifically, as shown in FIG. 4, the controller 130 may be communicatively coupled to the ground engaging member actuator 120 via a wired or wireless connection to allow control signals (e.g., indicated by dashed lines 138 in FIG. 4) to be transmitted from the controller 130 to the actuator 120. In this regard, the controller 130 may be configured to transmit control signals 138 to the actuator 120 instructing the actuator 120 to adjust the penetration depth of the ground engaging member 114, such as by extending or retracting the actuator's rod 122 relative to the corresponding cylinder 124, such that sensor penetration depth 128 corresponds to the selected planting depth. In one embodiment, the penetration depth of the ground engaging member 114 may be adjusted independently of the disc gang(s) 48 and/or the shank(s) 54. In this regard, the controller 130 may be configured to control the operation of the ground engaging member actuator 120 independently of the disc gang actuator(s) 104 and/or the shank actuator(s) 112.

In accordance with aspects of the present subject matter, the controller 130 may be configured to determine one or more soil parameters of the soil within the field across which the implement 10 is being moved at the selected planting depth. Specifically, as shown in FIG. 4, the controller 130 may be communicatively coupled to the sensor 126 via wired or wireless connection to allow sensor data (e.g., as indicated by dashed line 140 in FIG. 4) to be transmitted from the sensor 126 to the controller 130. In this regard, the controller 130 may be configured to determine or estimate the soil parameter(s) of the soil within the field at the selected planting depth based on the received sensor data 140. Such soil parameter(s) may be related to soil filth at the selected planting depth and include the amount or stability of soil aggregates at the selected planting depth, the degree of aeration at the selected planting depth, the presence and/or amount of residue at the selected planting depth, the amount of organic matter at the selected planting depth, the moisture content of the soil at the selected planting depth, and/or a temperature of the soil at the selected planting depth. For instance, the controller 130 may include a look-up table, suitable mathematical formula, and/or algorithms stored within its memory 134 that correlates the received sensor data 140 to the soil parameter(s). Additionally, in one embodiment, the controller 130 may be configured to generate a field map illustrating the determined soil parameter(s) at one or more locations within the field across which the implement 10 is being moved. Such field map may, in turn, be used during subsequent planting operations to set and/or adjust one or more operating parameters of the planting implements/equipment.

Furthermore, the controller 130 may be configured to monitor the determined soil parameter(s) and initiate one or more control actions when the soil parameter(s) exceeds or falls below a threshold soil parameter value(s). Specifically, in several embodiments, the controller 130 may be configured to compare the values associated with the monitored soil parameter(s) to an associated a threshold soil parameter value. Thereafter, in the event that the value(s) of the monitored soil parameter(s) exceeds or falls below the associated threshold soil parameter value (thereby indicating that the soil parameter may be too high or too low), the controller 130 may be configured to initiate one or more control actions.

In one embodiment, the controller 130 may be configured to notify the operator of implement 10 that the value(s) of the monitored soil parameter(s) has exceeded or fallen below the associated threshold soil parameter value. Specifically, in one embodiment, the controller 130 may be communicatively coupled to the user interface 102 via a wired or wireless connection to allow feedback signals (e.g., indicated by dashed line 142 in FIG. 4) to be transmitted from the controller 130 to the user interface 102. In such embodiment, the feedback signals 142 may instruct the user interface 102 to provide a notification to the operator of the implement 10 (e.g., by causing a visual or audible notification o r indicator to be presented to the operator) that provides an indication that the value(s) of the monitored soil parameter(s) has exceeded or fallen below the associated threshold soil parameter value. In such instances, the operator may then choose to initiate any suitable corrective action he/she believes is necessary, such as adjusting one or more operating parameters of the implement 10 and/or the work vehicle 12.

Moreover, in several embodiments, the controller 130 may be configured to automatically adjust one or more operating parameters of the implement 10 when it is determined that the value(s) of the monitored soil parameter(s) has exceeded or fallen below the associated threshold soil parameter value. Specifically, as shown in FIG. 4, the controller 130 may be communicatively coupled to the disc gang actuator(s) 104 and/or the shank actuator(s) 112 of the implement 10 via a wired or wireless connection to allow control signals 138 to be transmitted from the controller 130 to the actuator(s) 104 and/or the actuators 112. As such, the controller 130 may be configured to transmit control signals 138 to the actuator(s) 104 instructing the actuator(s) 104 to adjust the angle of the disc gang(s) 44 relative to the lateral centerline of the implement frame 28 and/or the penetration depth of the associated disc blade(s) 46. In addition, the controller 130 may be configured to transmit control signals 128 to the actuator(s) 112 instructing the actuator(s) 112 to adjust the penetration depth of the associated shank(s) 54.

Furthermore, in one embodiment, the controller 130 may be configured to automatically adjust the ground speed at which the work vehicle 12 is towing the implement 10 across the field when it is determined that the value(s) of the monitored soil parameter(s) has exceeded or fallen below the associated threshold soil parameter value. Specifically, the controller 130 may be communicatively coupled to the engine 24 and/or the transmission 26 of the work vehicle 12 via a wired or wireless connection to allow control signals 138 to be transmitted from the controller 130 to the engine 24 and/or the transmission 26. For example, the control signals 138 may be configured to instruct the engine 24 to vary its power output to increase or decrease the ground speed of the work vehicle 12 in a manner that adjusts the soil parameter(s) of the field. Similarly, the control signals 138 may be configured to instruct the transmission 26 to upshift or downshift to change the ground speed of the work vehicle 12 in a manner that adjusts the soil parameter(s) of the field. However, it should be appreciated that, in alternative embodiments, the controller 130 may be configured to transmit control signals to any other suitable component of the work vehicle 12 and/or implement 10 such that the ground speed of the work vehicle 12 and/or implement 10 is adjusted.

Figure 5:
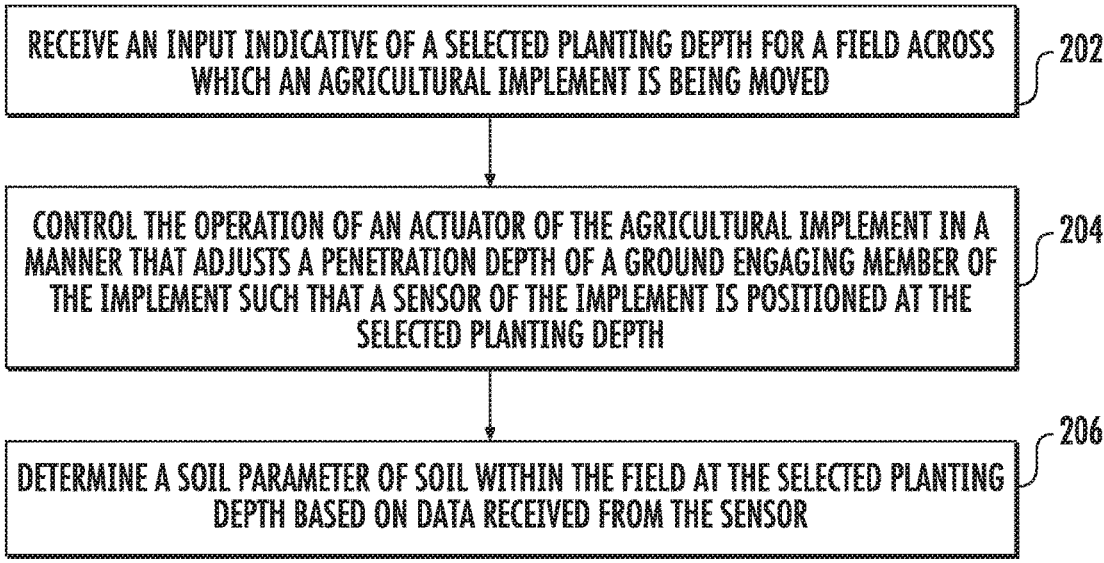
FIG. 5 illustrates a flow diagram of one embodiment of a method for determining soil parameters of a field across which an agricultural implement is being moved in accordance with aspects of the present subject matter Repeat use of reference characters in the present specification and drawings is intended to represent the same or analogous features or elements of the present technology.

Referring now to FIG. 5, a flow diagram of one embodiment of a method 200 for determining soil parameters of a field across which an agricultural implement is being moved is illustrated in accordance with aspects of the present subject matter. In general, the method 200 will be described herein with reference to the implement 10 and the system 100 described above with reference to FIGS. 1-4. However, it should be appreciated by those of ordinary skill in the art that the disclosed method 200 may generally be utilized to determine soil parameters of the field in connection with any agricultural implement having any suitable implement configuration and/or any system having any suitable system configuration. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (202), the method 200 may include receiving, with a computing device, an input indicative of a selected planting depth for a field across which an agricultural implement is being moved. For instance, as described above, the controller 130 may be communicatively coupled to the user interface 102. As such, the controller may be configured to receive operator input signals 136 that are indicative of a selected planting depth from the user interface 102.

Additionally, at (204), the method 200 may include controlling, with the computing device, the operation of an actuator of the agricultural implement in a manner that adjusts a penetration depth of a ground engaging member of the implement such that a sensor of the implement is positioned at the selected planting depth. For instance, as described above, the controller 130 may be communicatively coupled to the ground engaging member actuator 120. As such, the controller 130 may be configured to transmit controls signals 138 to the actuator 120 instructing the actuator 120 to adjust the penetration depth of a ground engaging member 114 of the implement 10 such that the sensor 126 is positioned at the selected planting depth.

Moreover, as shown in FIG. 5, at (206), the method 200 may include determining, with the computing device, a soil parameter of soil within the field at the selected planting depth based on data received from the sensor. For instance, as described above, the controller 130 may be communicatively coupled to the sensor 126. As such, when the implement 10 is being towed across the field by the work vehicle 12, the controller 130 may be configured to receive sensor data 140 from the sensor 126. Thereafter, the controller 130 may be configured to determine or estimate one or more soil parameters of the soil within the field across which the implement 10 is being moved at the selected planting depth based on the received sensor data 140.

It is to be understood that the steps of the method 200 are performed by the controller 130 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 130 described herein, such as the method 200, is implemented in software code or instructions which are tangibly stored on a tangible computer readable medium. The controller 130 loads the software code or instructions via a direct interface with the computer readable medium or via a wired and/or wireless network. Upon loading and executing such software code or instructions by the controller 130, the controller 130 may perform any of the functionality of the controller 130 described herein, including any steps of the method 200 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. A system for determining soil parameters of a field across which an agricultural implement is being moved, the system comprising:
   a ground engaging member configured to penetrate soil within the field;
   an actuator configured to adjust a penetration depth of the ground engaging member;
   a sensor mounted on the ground engaging member, the sensor configured to capture data indicative of a soil parameter of soil within the field;
   a controller communicatively coupled to the sensor, the controller configured to:
      receive an input indicative of a selected planting depth for the field;
      control an operation of the actuator in a manner that adjusts the penetration depth of the ground engaging member such that the sensor is positioned at the selected planting depth; and
      determine the soil parameter of the soil within the field at the selected planting depth based on the data received from the sensor;
      wherein the controller is further configured to monitor the soil parameter relative to a threshold soil parameter value and initiate a control action when the monitored soil parameter has exceeded or fallen below the threshold soil parameter value;
      wherein the control action comprises adjusting an operating parameter of the agricultural implement;
      wherein the operating parameter comprises a ground speed of the agricultural implement.

2. The system of claim 1, wherein the soil parameter comprises at least one of an amount of soil aggregates at the selected planting depth, a degree of aeration at the selected planting depth, a presence of residue at the selected planting depth, an amount of residue at the selected planting depth, an amount of organic matter at the selected planting depth, a moisture content of the soil at the selected planting depth, or a temperature of the soil at the selected planting depth.

3. The system of claim 1, further comprising:
   a ground engaging tool configured to penetrate the soil in a manner that performs an agricultural operation on the soil within the field, wherein a penetration depth of the ground engaging tool is independent of the penetration depth of the ground engaging member.

4. The system of claim 1, wherein the control action comprises notifying an operator of the agricultural implement that the monitored soil parameter has exceeded or fallen below the threshold soil parameter value.

5. The system of claim 1, further comprising:
   a ground engaging tool configured to penetrate the soil in a manner that performs an agricultural operation on the soil within the field, the operating parameter comprising a penetration depth of the ground engaging tool.

6. The system of claim 1, further comprising:
   a disc gang, the operating parameter comprising an angle of the disc gang.

7. The system of claim 1, wherein the controller is further configured to generate a field map illustrating the soil parameter at one or more locations within the field.

8. The system of claim 1, wherein the sensor comprises at least one of a multispectral sensor, an optical sensor, or a dielectric sensor.

9. A method for determining soil parameters of a field across which an agricultural implement is being moved, the agricultural implement including a ground engaging member and a sensor mounted on the ground engaging member, the method comprising:
   receiving, with a computing device, an input indicative of a selected planting depth for the field;
   controlling, with the computing device, an operation of an actuator in a manner that adjusts a penetration depth of the ground engaging member such that the sensor is positioned at the selected planting depth;
   determining, with the computing device, a soil parameter of soil within the field at the selected planting depth based on data received from the sensor;
   monitoring, with the computing device, the soil parameter relative to a threshold soil parameter value; and
   when the monitored soil parameter exceeds or falls below the threshold soil parameter value, imitating, with the computing device, a control action;
   wherein the control action comprises adjusting an operating parameter of the agricultural implement;
   wherein the operating parameter comprises a ground speed of the agricultural implement.

10. The method of claim 9, wherein the soil parameter comprises at least one of an amount of soil aggregates at the selected planting depth, a degree of aeration at the selected planting depth, a presence of residue at the selected planting depth, an amount of residue at the selected planting depth, an amount of organic matter at the selected planting depth, a moisture content of the soil at the selected planting depth, or a temperature of the soil at the selected planting depth.

11. The method of claim 9, wherein the control action comprises notifying an operator of the agricultural implement that the monitored soil parameter has exceeded or fallen below the threshold soil parameter value.

12. The method of claim 9, wherein the operating parameter comprises a penetration depth of a ground engaging tool of the agricultural implement.

13. The method of claim 9, wherein the operating parameter comprises an angle of a disc gang of the agricultural implement.

14. The method of claim 9, further comprising:
generating, with the computing device, a field map illustrating the soil parameter at one or more locations within the field.

* * * * *